United States Patent [19]

Vlasbloem et al.

[11] Patent Number: 4,715,056
[45] Date of Patent: Dec. 22, 1987

[54] APPARATUS FOR SLIT RADIOGRAPHY

[75] Inventors: Hugo Vlasbloem, Maasland; Simon Duinker, Bloemendaal, both of Netherlands

[73] Assignee: bv Optische Industrie"De Oude Delft", Delft, Netherlands

[21] Appl. No.: 713,198

[22] Filed: Mar. 18, 1985

[30] Foreign Application Priority Data

Mar. 16, 1984 [NL] Netherlands ................. 8400845

[51] Int. Cl.$^4$ ............................................. G21K 1/04
[52] U.S. Cl. ................................... 378/152; 378/145; 378/146; 378/147; 378/150; 378/153
[58] Field of Search ............................. 378/145–148, 378/150–153, 156–158

[56] References Cited

U.S. PATENT DOCUMENTS

| | | | |
|---|---|---|---|
| 2,996,267 | 8/1961 | Warren | 188/267 |
| 3,101,407 | 8/1963 | Shipman, Jr. | 378/146 |
| 3,402,292 | 9/1968 | Baecklund | 378/157 |
| 3,660,664 | 5/1972 | Pasmeg | 378/159 |
| 3,755,672 | 8/1973 | Edholm et al. | 378/151 |
| 4,132,895 | 1/1979 | Froggatt | 378/146 |
| 4,137,460 | 1/1979 | Fitzsimmons et al. | 378/151 |
| 4,442,538 | 4/1984 | Haendle | 378/146 |

FOREIGN PATENT DOCUMENTS 2345406  7/1975  Fed. Rep. of Germany ...... 378/150

OTHER PUBLICATIONS

"Computer Assisted Exposure in Scanned Film Radiography" by D. B. Plewes Proceedings Int. Workshop on Physics & Eng in Med. Imaging, Mar. 1982.
"Digitally Controlled Beam Attenuator" by Peppler et al., SPIE vol. 347, Application of Optical Instrumentation in Medicine C, 1982.

Primary Examiner—Craig E. Church
Assistant Examiner—John C. Freeman
Attorney, Agent, or Firm—Louis E. Marn

[57] ABSTRACT

An apparatus for slit radiography comprising an X-ray source, an X-ray detector positioned behind a body being irradiated, said detector collecting the radiation passed through the body, and a slit diaphragm placed between the X-ray source and the body being irradiated, through which diaphragm there is formed a planar X-ray fan beam, while for obtaining a complete X-ray shadow image of the desired part of the body at least the fan beam performs a scanning movement. There are provided detection means coacting with the X-ray detector and comprising a plurality of sections juxtaposed in the longitudinal direction of the strip-like portion of the X-ray detector irradiated through the slit diaphragm, each section being adapted to produce an electric signal depending upon the radiation impinging instantaneously on the associated section of the X-ray detector. The slit diaphragm comprises a plurality of sections juxtaposed in the longitudinal direction of the slit, each coacting with at least one controllable attenuation element and corresponding with the number of sections of the detection means, and is provided with control means which during the scanning movement instantaneously and simultaneously adjust the quantity of X-rays passed per section of the diaphragm, under the control of the electric signals generated by the detection means.

26 Claims, 15 Drawing Figures

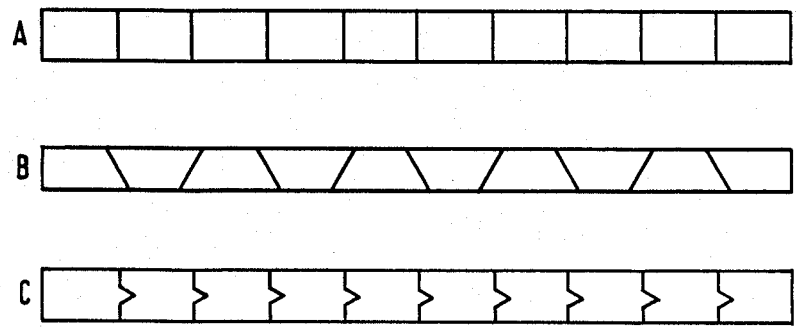
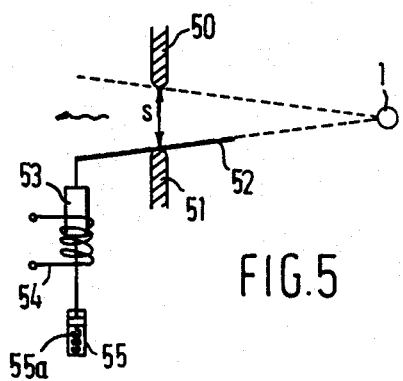
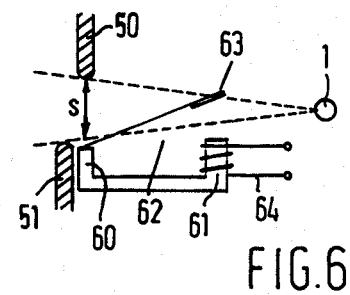
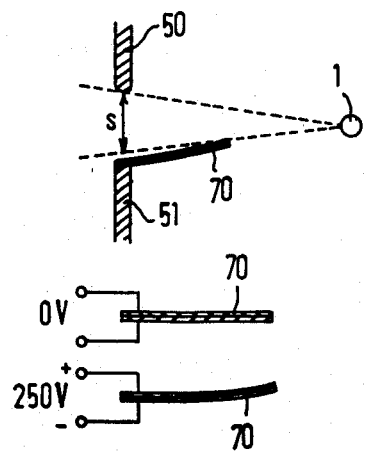
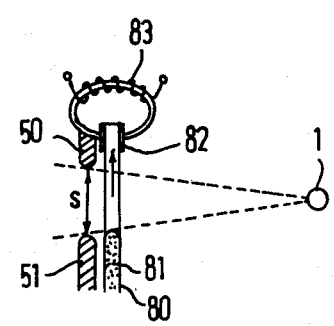
FIG.4
FIG.5
FIG.6
FIG.7
FIG.8

APPARATUS FOR SLIT RADIOGRAPHY

The present invention relates to an apparatus for slit radiography comprising an X-ray source, an X-ray detector disposed behind a body being irradiated, said detector collecting the radiation passed through the body, and a slit diaphragm interposed between the X-ray source and the body being irradiated, through which diaphragm there is formed a planar X-ray fan beam, while for obtaining a complete X-ray shadow image of the desired part of the body, at least the fan beam performs a scanning movement. A similar apparatus is disclosed e.g. in Dutch patent application No. 83.03156.

The known apparatus comprises an elongate X-ray detector placed in such a manner that the entrance surface thereof always collects the radiation passed through the slit diaphragm and the body being irradiated. The assembly of detector, X-ray source, and diaphragm are moved relatively to the body in such a manner that the desired part thereof is scanned. The detector converts the X-rays collected into an intensified light image, which is used for exposing a photographic film.

It is observed that the present invention can also be used when a different type of detector is employed. The detector could be arranged, for example to provide instead of a light image, electric signals representing an image.

Also, the detector may be so dimensioned that it can remain stationary, while the fan beam performs a scanning movement. This will be further explained hereinafter. Besides, the present invention can also be utilized when the output image of the detector is picked up with a video camera.

In general, the present invention can be used in any situation wherein for forming an X-ray shadow image, a planar X-ray fan beam scans a body being irradiated over a given range.

A problem encountered in the apparatus known from Dutch patent application No. 83.03156 and in other known apparatus is that a compromise is necessary between contrast sensitivity and contrast range of the shadow image to be formed. In thorax photography e.g. it is not quite well possible to display both the soft parts, such as the lungs and the abdomen, and the hard parts, such as the ribs and spine in such a manner that small differences in contrast are visible in both the soft and the hard parts. Furthermore first a measuring stroke is necessary for adjusting the X-ray source.

It is an object of the present invention to eliminate the above problem. To this effect according to the invention, an apparatus of the above described type is characterized in that there are provided detection means co-acting with the X-ray detector and comprising a plurality of sections juxtaposed in the longitudinal direction of the strip-like portion of the X-ray detector irradiated through the slit diaphragm, each section being adapted to produce an electric signal depending upon the radiation impinging instantaneously on the associated section of the X-ray detector; and that the slit diaphragm comprises a plurality of sections juxtaposed in the longitudinal direction of the slit, each coacting with at least one controllable attenuation element, and corresponding with the number of sections of the detection means, and is provided with control means which during the scanning movement instantaneously and simultaneously adjust the quantity of X-rays passed per section of the diaphragm, under the control of the electric signals generated by the detection means.

It is observed that efforts have already been made in the past to remove the above problem.

The article "Computer assisted exposure in scanned film radiography" by D. B. Plewes in Proceedings International Workshop on Physics and Engineering in Medical Imaging, March 1982, pp. 79 ff. discloses a method of image harmonization in slit radiography. According to the article, to this effect the moving slit diaphragm coacts with a second moving slit diaphragm which is placed transverse to the first, so that a relatively small moving diaphragm is produced of more or less rectangular or diamond-shaped configuration. Consequently, the body being irradiated is scanned, in fact, according to the flying-spot system.

An X-ray film cassette is placed behind the body being irradiated. Behind the cassette there is positioned a detector which measures the radiation passing through the film cassette instantaneously. Depending on the value measured, the adjustment of the X-ray source and thereby both the intensity and the X-ray spectrum are controlled.

Although the Plewes article therefore, like the present invention, relates to dynamic image harmonization, the method described in the Plewes article is based on a different basic idea, since it does not concern local adjustment of the slit width of the diaphragm at a given setting of the X-ray source.

A further drawback going with the technique disclosed in the above article is that an expensive controllable X-ray source is required. Another drawback is that by application of the flying-spot system, the effective use of the X-rays generated is slight, because the major part of the radiation is suppressed by the coacting moving slit diaphragm. For obtaining a usable quantity of radiation through the relatively small resulting diaphragm aperture, consequently, an overdimensioned X-ray source is required. Moreover, relatively long scanning times will be necessary.

Furthermore, in the technique disclosed in the article, measurement takes place behind the film cassette, so that the X-ray spectrum is affected, with the result that the control of the X-ray source adjustment is not optimum for parts of the patient that cause little attenuation of the X-rays.

Reference is also made to the article "Digitally controlled beam attenuator" by Peppler et al., published in SPIE, vol. 347, Application of Optical Instrumentation in Medicine C, 1982, pp. 106 ff., describing a method of obtaining a harmonized X-ray shadow image. According to the technique described by Peppler et al., use is made of a matrix of attenuation elements, the attenuation of which can be adjusted individually. After adjustment of the attenuation of the elements, a patient is X-rayed. The Peppler method therefore does neither concern slit radiography nor dynamic image harmonization and moreover is time-consuming.

Some embodiments of the apparatus according to the invention will now be described, by way of example, with reference to the accompanying drawings, in which:

FIG. 1 is a diagrammatic side view of an embodiment of an apparatus for slit radiography according to the present invention;

FIGS. 2a and 2b diagrammatically show an embodiment of a slit diaphragm which can be used in the apparatus shown in FIG. 1;

FIG. 4 shows some embodiments of a slit diaphragm shown in FIGS. 2a and 2b;

FIG. 5 shows a slit diaphragm and the manner in which the effective slit width can be controlled locally;

FIGS. 6, 7 and 8 show variants of FIG. 5;

Figure 1:
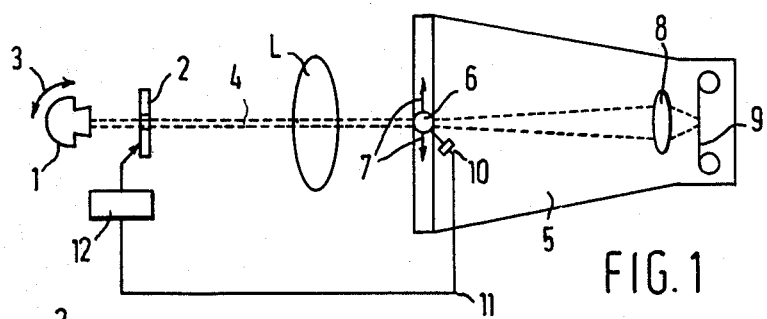

FIG. 1 is a diagrammatic side view of an embodiment of an apparatus for slit radiography comprising an X-ray source 1 which together with a slit diaphragm 2 is adapted to perform a swivelling movement, as indicated by an arrow 3. Through the slit diaphragm there is produced a planar X-ray fan beam 4 which, when the X-ray source and the slit diaphragm perform the swivelling movement indicated by arrow 3, effects a scanning movement.

It is observed that a scanning movement of the X-ray source can also be obtained when the X-ray source is stationary and the slit diaphragm performs a translational movement transversely to the longitudinal direction of the slit, possibly accompanied by a swivelling movement, or when the diaphragm is stationary and the X-ray source performs a translational and possibly a swivelling movement.

Opposite the slit diaphragm a casing 5 is positioned at such an interspace that there remains room for a body L being irradiated, said casing containing an X-ray detector 6 having an entrance face sufficiently large to collect the radiation passing at any moment through the body being irradiated during the swivelling movement of the X-ray source and the slit diaphragm.

In the embodiment shown, in the manner as described e.g. in Dutch patent application No. 83.03156, an elongate tubular detector of the proximity focus type is employed which converts the X-rays collected into a light image, thereby effecting a vertical movement in synchronism with the swivelling of the X-ray source, as indicated by arrows 7.

The instantaneous strip-like light image provided by the detector is projected on a film 9 by means of a lens system 8, shown diagrammatically, for forming a complete image from the successively projected strip-like images.

According to the present invention there is positioned adjacent the X-ray detector 6 a light detection device 10 which, as viewed in a direction transverse to the plane of drawing, comprises a plurality of juxtaposed sections, each measuring the quantity of light generated by a corresponding opposite portion of the exit face of the X-ray detector: For this purpose, in the embodiment shown, the light detection device moves along with the X-ray detector. The quantities of light measured by the sections of the light detection device are converted in known manner into electric signals which are supplied simultaneously through lead 11 to control means 12, shown diagrammatically. The control means are adapted to locally adjust the width and/or the transmissivity to X-rays of the slit diaphragm, for which purpose the slit diaphragm consists of a plurality of sections corresponding with the number of sections of the light detection device. The slit width and/or the transmissivity characteristic of each of the diaphragm sections can be adjusted separately by one of the methods to be described.

The adjustment of the diaphragm sections is effected according to the present invention during X-raying, so that a dynamic instantaneous exposure control is achieved and the film 9 can be exposed in an optimum manner at any moment. An additional advantage is that there is thus obtained a noise equalization, so that the signal-to-noise ratio is substantially constant throughout the entire image, which is especially of importance when digital techniques of X-ray diagnostics are used.

Naturally, the light detection device is placed in such a manner that this does not interfere with the passage of rays between the X-ray detector 6 and the lens system 8.

Figure 2A:
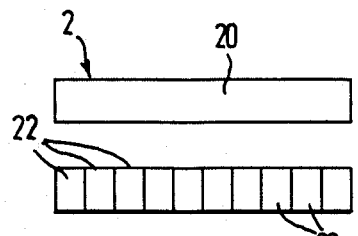

FIG. 2a diagrammatically shows an embodiment of a slit diaphragm for an apparatus according to the present invention. The diaphragm comprises an upper portion 20, which may be made of lead, and a lower portion 21, which comprises sections 22 slidable relatively to each other in the direction of the upper portion. Sections 22 may also be made of lead.

Figure 2B:
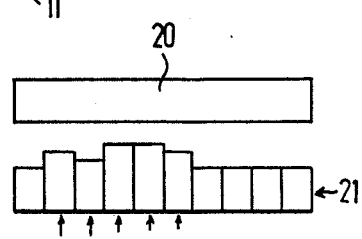

FIG. 2b shows a possible position of the slidable sections 22 at a given moment during X-raying. The sections indicated by arrows have been shifted in the direction of the upper portion of the diaphragm so as to reduce the slit width of the diaphragm at that location.

The extent of shift at some particular moments depends on the quantity of light measured by the corresponding section of the light detection device 1.

In the embodiment shown, ten slidable sections are used that correspond with ten light detection sections.

In thorax radiography, a satisfactory result can be obtained with such a number of sections. If desired, a different number of sections can of course be used.

Figure 3:
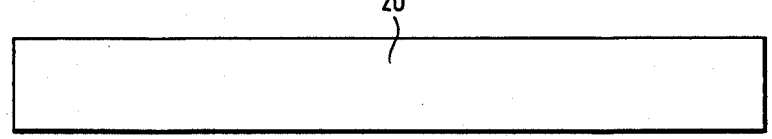
FIG. 3 shows in what manner the slit diaphragm shown in FIGS. 2a and 2b can be controlled.

FIG. 3 diagrammatically shows in what manner the sections of the slit diaphragm shown in FIG. 2 can be controlled. The sections of the diaphragm portion 21 are each connected by means of a stationary member 30, e.g. a small rod, to a coil core 31, e.g. of soft iron, which is adapted to slide in a coil 32, and which can be maintained in the rest portion by resetting means, such as spring means 31a or a magnet.

Each coil is energized by an output 33 of a control device 34. The control signal appearing at each output 33 depends on an input signal appearing at a corresponding input 35 of the control device and originating from the associated section of the light detection device. The current intensity through a coil determines the position of the associated soft iron core and hence the position of the diaphragm section coupled therewith.

It is observed that in the embodiment shown, only one of the members of the slit diaphragm has slidable sections. Naturally, it is also possible to provide both members of the slit diaphragm with slidable sections. It is further noted that the slidable sections of a diaphragm member are placed jointly in a supporting member. The construction of such a supporting member is obvious to one skilled in the art and hence will not be described herein.

The slidable sections of the one member of the slit diaphragm shown in FIGS. 2 and 3 may have a rectangular cross-sectional configuration, as shown in FIG. 4A, showing a cross-section on the line IV—IV of FIG. 3. In that case interspaces or transitions between the sections could lead to a line effect in the eventual radiograph. In order to reduce the chance thereof, the sections of the slit diaphragm may each be trapezoidal in cross-section, as shown in FIG. 4B, showing a cross-section corresponding with that of FIG. 4A. Other variants are conceivable too, e.g. as shown in FIG. 4C, wherein the sections engage with each other by means of a tongue and groove joint.

FIG. 5 shows a diagrammatic side view of a different embodiment of a slit diaphragm which can be employed in an apparatus according to the present invention and which is based on two stationary diaphragm members 50, 51 defining a stationary slit S. For the purpose of orientation, FIG. 5 shows the X-ray source 1 diagrammatically.

The slit S contains a plurality of juxtaposed elongate attenuation elements, one of which is shown at 52 in FIG. 5. Attenuation element 52 extends through the slit S and is adapted to pivot relatively to one of the stationary diaphragm portions, in this embodiment the lower portion 51, or relatively to a suitably placed carrier. Adjacent the one end of the attenuation element 52, in the same manner as described for the sections shown in FIG. 3, this is coupled with a slidable soft iron core 53 of a coil 54. The soft iron core is further connected to an attenuation element 55 adapted to prevent the core 53 from slipping upon energization of the coil. Besides, a return spring is provided, in this embodiment a compression spring 55a, placed in the attenuation element.

In this embodiment, the other end of the attenuation element 52 points to the X-ray source and, by control of the coil 54, can extend into the X-ray beam through the slit S to a greater or lesser extent, in order to intercept the same at least partly.

The attenuation elements may be made of lead, but also of other suitable material attenuating X-radiations, as e.g. soft iron, bronze, gold etc.

FIG. 6 shows a variant of FIG. 5. In the embodiment shown in FIG. 6, the stationary members of the slit diaphragm are again indicated at 50 and 51. Between the X-ray source 1 and the slit diaphragm there is placed a U-shaped yoke of soft iron, one leg 60 of which lies adjacent the slit diaphragm and the other leg 61 is spaced apart therefrom. Attached to the top of the one leg 60 is a resilient tongue 62, which extends obliquely upwards and carries at the other end a plate of magnetic material, e.g. magnet steel, disposed above the other leg 61. Besides, a coil 64 energizable by a control device, comparable to the control device 34 of FIG. 3, is wound about leg 61. Depending on the control of coil 64, the plate 63 is attracted to a greater or lesser extent by the leg 61 and the plate attenuates the X-radiation passed through slit S to a greater or lesser extent.

It is observed that for controlling the slit width along the entire length of slit S, a plurality of such yokes having resilient tongues as described, are juxtaposed.

It is further observed that in principle the yoke could be placed in such a manner that the leg having the coil 64 is disposed adjacent the diaphragm and the resilient tongue is attached to the leg spaced apart from the diaphragm.

Furthermore, in both cases the yoke may be positioned at the other side of the diaphragm, i.e. the side away from the X-ray source.

When use is made of sliding elements, as shown in FIGS. 2–4, or of elongate elements as shown in FIGS. 5 and 6, the instantaneous position thereof can also be controlled by a miniature stepping motor having an eccentric connected to the element to be controlled by means of e.g. a rod. Each element then requires a stepping motor. The control signals for the stepping motor are provided by the control means 12. It is true that when stepping motors are used, only a number of discrete positions of the attenuation elements can be adjusted, but this number may be sufficiently large, e.g. one hundred, to ensure satisfactory operation.

Figure 14:
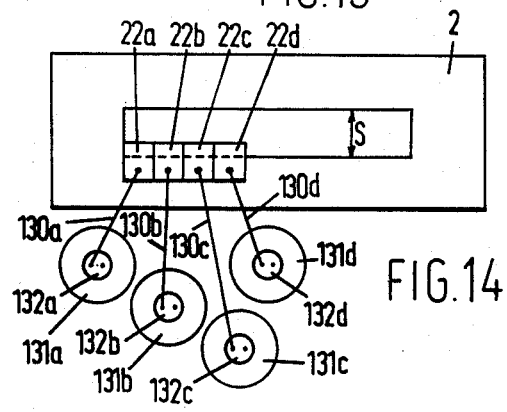
FIG. 14 shows still another embodiment of the present invention.

FIG. 14 illustrates diagrammatically the use of stepping motors for controlling slide shaped attenuation elements. For the sake of clearness, FIG. 14 only shows four elements 22a–22d coacting with the slit of the slit diaphragm 2. Each element is eccentrically coupled with the shaft of a stepping motor 131a–131d by means of a rigid connecting member 130a–130d e.g. a rod, or with a disc or cam 132a–132d disposed on the shaft. The rotation of the shaft of the stepping motor is thus converted through the eccentrically connected rod into a sliding movement of the associated attenuation element.

FIG. 7 shows a different variant of FIG. 5. Attached to at least one of the stationary members of the slit diaphragm or to a suitable carrier are a plurality of juxtaposed, rod-shaped piezoelectric elements, one of which is indicated at 70. Such an element is straight in the rest position, but when a voltage is applied between opposite sides, the element is curved, which is shown in FIG. 7. Use can be made of this known effect for varying the slit width of the slit diaphragm in a controllable manner.

Such elements are available under the name of Bimorph Flexure Element. Since such elements mostly contain lead, they can be conveniently employed for the object in mind. If the attenuating effect, however, is insufficient, the piezoelectric elements can be coated with material absorbing X-rays.

FIG. 8 shows a different variant wherein a magnetic liquid is used for adjusting the slit width of the slit diaphragm.

Between the X-ray source 1 and the slit diaphragm there is positioned a plurality of juxtaposed planar hollow tubes 80 of synthetic plastics material or glass containing a known per se magnetic liquid 81.

At the top of each tube there are positioned pole pieces 82 connected by a coil core about which a coil 83 is wound. On energization of the coil, the magnetic liquid is attracted by the pole pieces and the liquid moves to before the slit S, so that the radiation from X-ray source 1 is attenuated locally.

Figure 9:
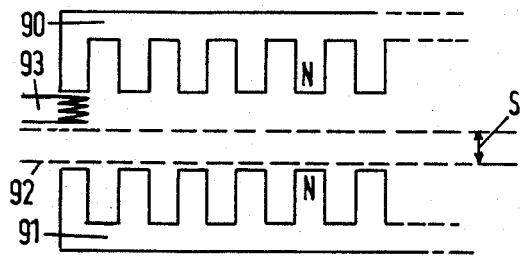
FIGS. 9-11 show another embodiment of a controllable slit diaphragm according to the present invention.

Still another embodiment of attenuation means which in a controlled manner can locally attenuate X-radiation passed, or to be passed, through a slit diaphragm to a greater or lesser extent is shown in FIG. 9.

FIG. 9 shows two rows of magnet poles 90, 91 extending parallel to the slit of a slit diaphragm before or behind the slit diaphragm. The slit of said diaphragm is shown at 92 in broken lines. The rows of magnet poles are arranged in such a manner that two north poles or two south poles are always opposite to each other. The poles can be formed by permanent magnets or by means of electric magnets. Between each pair of opposite poles there is disposed a small light coil, e.g., of copper wire, the length of which corresponds with the thickness of the X-ray beam adjacent the rows of magnet poles. FIG. 9 shows only one coil 93 for the sake of clearness. By controlling the direction and the intensity of the current through a coil 93, the position of a coil between the two opposite magnet poles can be adjusted and varied. The copper wire of the coil absorbs substantially all hard and a major portion of the soft X-radiation, so that by means of a configuration shown in FIG. 9 it is possible to attenuate the X-rays passed through slit S in an effective and controllable manner.

Figure 10:
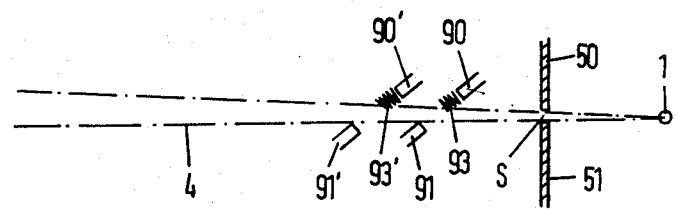

Since there necessarily remains an interspace between juxtaposed coil 93 through which therefore unattenuated X-radiation could pass, preferably at least two of the configurations shown in FIG. 9 are positioned in offset tandem relationship. This is diagrammatically shown in FIG. 10. A second pair of rows of magnet poles 90', 91' with associated coils 93' is positioned behind a first pair of rows of magnet poles 90, 91 with coils 93. The magnet poles and the coils in FIG. 10 are arranged slightly inclined relatively to the X-ray beam 4, so that each coil produces an elliptical shadow and the extent of attenuation can be controlled more accurately. FIG. 10 shows in full lines 94 the shadow of the first row of coils (if said coils all extend equally far into the X-ray beam), while the shadow of the second row of coils is shown in broken lines 95.

Figure 11:
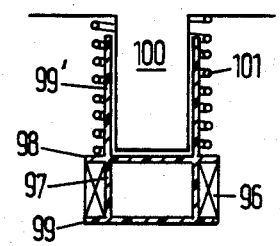

FIG. 11 shows a practical embodiment of a coil usable as an attenuation element. A plurality of windings 96 is wound about a sleeve 97 between two flanges 98, 99. The sleeve is extended on one end beyond the flange 98 and the extended portion 99' is pushed about an associated magnet pole 100, which belongs to one of the rows of magnet poles, so that the movement of the coil is conducted.

The coil is adapted for coaction with stop means defining the extreme positions of the coil, for which purpose could be used the two flanges 98, 99, which for example could strike against the corresponding magnet poles in the two extreme positions. This function could also be performed by the free end of the extended sleeve portion 99' and the flange 99.

Furthermore, a return spring can be used, as indicated by way of example at 101. If the position shown in FIG. 11 is the rest position, the spring 101 is a tension spring, and if the position shown in FIG. 11 is the extreme position, the spring 101 is a compression spring.

Experiments have shown that it is not necessary to position each coil between two magnet poles but that a single magnet pole for each coil is sufficient. Besides, the return force for a coil can be the coil's own weight, if the direction of movement of the coil has a sufficiently large vertical component.

Consequently, in a preferred embodiment, a single row of magnet poles disposed above the X-ray beam to be attenuated will be sufficient, the coil associated with each magnet pole in a rest position is underneath the X-ray beam, which in operation, can be drawn into the X-ray beam to a greater or lesser extent.

It is observed that in the embodiments shown, the slit width may vary stepwise along the length of the slit, as can be seen e.g. in FIG. 2b. This could sometimes be objectionable. However, it is possible to divide the slidable sections of FIGS. 2, 3 and 4 or the attenuation elements of FIGS. 5, 6 and 7 into groups of an odd number, with only the central section or the central element of each group being controlled by the control means, while each section or each element is resiliently connected to the adjoining elements. Thus, a more gradual variation of the slit width, seen in the length of the slit, can be achieved.

It is noted that only examples have been given in the above of methods for locally varying the effective slit width of a slit diaphragm. Other methods will readily occur to one skilled in the art after reading the foregoing. For instance, it is possible to have a number of attenuation elements coact with each section of the slit diaphragm to be controlled, each introducing a predetermined attenuation factor.

Depending on the attenuation required for a given section, one or more attenuation elements can be pushed in front of the slit at that location to provide for the desired attenuation factor. This and other modifications are deemed to lie within the scope of the present invention.

In the embodiment of an apparatus for slit radiography shown in FIG. 1, an elongate proximity-focus tube is employed as an X-ray detector. Such a tube comprises an elongate cathode provided in known manner with a material converting X-radiation into light quanta, and with a material responsive to light quanta by releasing electrons. These electrons are drawn through an electric field to an anode parallel to the cathode and likewise strip-like, which forms a light image under the influence of the incoming electrons.

The light detection device may consist of a series of photosensitive elements placed in the housing of the X-ray detector but which may also be disposed exteriorly of the housing, in which case the light detection device may consist of a series of lenses, each viewing a section of the anode, and each followed by a photomultiplier tube.

It is also possible to accelerate the electrons released from the cathode of the X-ray detector in such a manner that a matrix of charge-coupled elements (CCDs) can be used as the anode. These CCDs provide direct electric output signals which can be used on the one hand for locally controlling the slit width and on the other hand for constructing the desired image e.g. by means of a computer, in which case the lens system 8 and the film 9 are unnecessary.

The present invention can also be used in an apparatus for slit radiography that does not comprise a detector moving along with the swivelling motion of the X-ray source and the slit diaphragm, but instead has a large X-ray screen that is exposed by the X-ray source with a scanning movement. In that case, the light detection device should make a scanning movement correponding with the swivelling movement of the X-ray source at the back of the X-ray screen. As an alternative, the light detection device can be formed e.g. by vertically arranged strip-like photoconductors which absorb little X-radiation and are disposed at the front of the X-ray screen where, in fact, light is produced as well.

Figure 12:
FIGS. 12, 13 show a further elaboration of the present invention.
Figure 12:
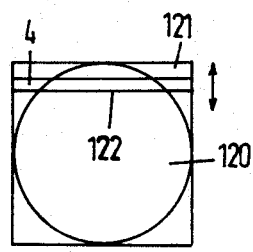

Such a solution is particularly suitable when the large X-ray screen is the screen of an existing stationary X-ray image intensifier. Such an intensifier mostly has a round entrance window. The idea underlying the present invention offers the possibility of reducing the load of radiation on the patient in that case. This will be further explained with reference to FIG. 12.

The entrance window 120 of the X-ray image intensifier tube has a surface scanned stripwise by the planar X-ray fan beam 4. Beam 4 scans a rectangular surface 121, while in general X-ray image intensifier tubes have a circular entrance window, as a result of which portions of a body being irradiated are unnecessarily exposed to X-radiation, which, true, irradiates the body but does not impinge upon the entrance window. This unnecessary radiation load can be prevented as follows.

Through lead 11 (FIG. 1) signals are applied to the control means 12 so that sections of the slit diaphragm can be completely closed in such a manner that at any moment of the scanning, the length of the non-closed portion of the slit diaphragm corresponds with the length of the strip 122 of the entrance window being scanned at that moment. The said signals may originate from a set of sensors sensing the form of the entrance window in synchronism with the scanning movement. The form of the entrance window may also be stored as a function of the scanning movement in digital form in a memory. During the scanning movement, said memory is read out and a computer computes the required length of the slit diaphragm, generating the required signals for the control means 12.

The control means 12 in that case may, in addition to elements defining the slit width, be connected to similar elements defining the slit length.

Particularly advantageous embodiments of elements for adjusting the length of the slit diaphragm are obtained by using the elements shown in FIGS. 5, 6, 7 for defining the length of the slit diaphragm.

Figure 13:
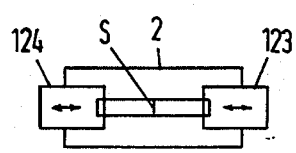

These figures should not be considered then to be a side view but a top view of the slit diaphragm, while such an element is present at each end of the slit. Also the two elements shown in FIG. 2 can be used for the same purpose. At each end of the slit there is provided such a sliding element, which may be made e.g. of lead. The latter embodiment is diagrammatically shown in FIG. 13, indicating the sliding elements at 123 and 124.

If a light tight film cassette is placed directly behind the X-ray screen, use can also be made of a light detection device placed at the front of the X-ray screen, or, again, an X-ray detector placed behind the film cassette for performing a scanning movement and provided with a light detection device as described hereinbefore, or a second large X-ray screen converting the X-rays passed through the film cassette into light and which is followed by a light detection device performing a scanning movement. On the other hand, the above mentioned drawback then occurs that the film cassette affects the X-ray spectrum, but the advantage of the local control of the slit width of the slit diaphragm is preserved.

The present invention can also be employed when the scanning movement takes place by rotation instead of by a linear movement transversely to the longitudinal direction of the slit.

All such modifications are deemed to fall within the scope of the present invention.

What we claim:

1. An apparatus for slit radiography, which comprises:
    an X-ray source;
    an X-ray detector for collecting radiation passing through a body to be radiographed;
    a slit diaphragm positioned between said X-ray source and said body for forming a substantially planar X-ray beam;
    a plurality of attenuating elements positioned along said slit diaphragm forming a plurality of attenuating sections;
    means for scanning said body with said planar X-ray beam;
    detection means cooperating with saisd X-ray detector and comprising a plurality of response sections juxtaposed along a direction of said slit diaphragm, each of said response sections being responsive to radiation collected on said X-ray detector to produce an electric signal representative of intensity of thus collected radiation, each of said response sections of said detection means corresponding to a respective attenuating section of said plurality of attenuating sections; and
    means for simultaneously controlling each of said attenuating sections during scanning of said body in response to said electric signal produced at a respective response section of said detection means.

2. The apparatus as defined in claim 1 wherein said attenuating elements comprise a plurality of juxtaposed elements slidable relatively to each other in a direction transverse to said slit diaphragm, each of said attenuating elements being mounted to a slidable core of a coil energized by said control means.

3. The apparatus as defined in claim 2, wherein said attenuating elements are trapezoidal in cross-section.

4. The apparatus as defined in claim 2 wherein said attenuating elements engage each other by means of a tongue and groove joint.

5. The apparatus as defined in claim 2 wherein said attenuating elements include a central element and side elements resiliently connnected to said central element, said central element being controlled by said control means.

6. The apparatus as defined in claim 1 wherein each attenuating element includes one elongate element extending substantially transversely to a longitudinal direction of said slit diaphragm so that one end thereof is moved into said planar X-ray beam in response to said control means.

7. The apparatus as defined in claim 6 wherein each of said elongate elements are hinged between ends thereof to a member of said slit diaphragm or to a carrier extending parallel thereto and wherein at least some of the elements are each connected adjacent the other end to a slidable core of a coil energized by the control means.

8. The apparatus as defined in claim 7 wherein said attenuating elements include a central element and side elements resiliently connected to said central element, said central element being controlled by said control means.

9. The apparatus as defined in claim 6 wherein said attenuating elements comprise a resilient tongue attached at one end to a leg of a U-shaped coil core and having at another end a plate of magnetic material extending above the other leg of said U-shape ooil core.

10. The apparatus as defined in claim 9 wherein each resilient tongue mounted to a U-shaped coil core is connected resiliently to adjoining elongate and similarly oriented elements unresponsive to a U-shaped coil core.

11. The apparatus as defined in claim 6 wherein each of said elongate attenuating elements is a piezoelectric element, said piezoelectric element being curved in response to a voltage applied by said control means so that free end of said piezoelectric element reduces the effective slit width of said slit diaphragm.

12. The apparatus as defined in claim 6 wherein a free end of each elongate element is coated with a material for attenuating X-ray radiation.

13. The apparatus as defined in claim 1 wherein each attenuating element is a tube bridging said slit diaphragm and partly filled with a magnetic liquid having a portion to be drawn into said bridging portion by a magnetic field produced in response to an electric magnet energized by said control means.

14. The apparatus as defined in claim 1 wherein said X-ray detector is an elongate image intensifier tube of a proximity type moving in synchronism with scanning movement of said X-ray source and slit diaphragm, said iamge intensifier tube converting X-rays into a light image; and wherein said detection means comprises a series of photosensitive elements coupled to said elongate image intensifier tube, each viewing an associated portion of light image to produce an electric signal proportional to instantaneously collected quantity of light.

15. The apparatus as defined in claim 14 wherein a series of photosensitive elements are disposed in said elongate image intensifier tube.

16. The apparatus as defined in claim 1 wherein said X-ray detector is an elongate image intensifier tube of the proximity type comprising a matrix of charge-coupled devices as an anode, output signals of which are applied on one hand to said control means and on another hand to a processing device for forming said desired image.

17. The apparatus as defined in claim 1 wherein said X-ray detector is a stationary X-ray screen scanned in synchronism with scanning of said X-ray source and slit diaphragm by means of a photosensitive detector comprising a plurality of judxtaposed sections.

18. The apparatus as defined in claim 1 wherein said X-ray detector is a stationary X-ray screen coupled to a film cassette in a light-tight manner; and further including a second X-ray detector positioned behind said film cassette for collecting X-rays instantaneously passing through said film cassette to convert the same into corresponding quantities of light measured by means of a series of photosensitive elements in synchromism with scanning of the X-ray source and slit diaphragm and converted into corresponding electric signals.

19. The apparatus as defined in claim 1 wherein each attenuating section is comprised of a plurality of attenuating elements arranged in tandem each having a predetermined attenuation factor for X-radiation and wherein said control means are operative for selectively sliding said in tandem attenuating elements in dependence on a signal generated by said detection means.

20. The apparatus as defined in claim 1 wherein said X-ray detector is a stationary X-ray screen, and wherein said detection means is comprised of juxtaposed strips of photocondutive material absorbing small amounts of X-radiation and disposed at a side of said X-ray screen proximal to said body being radiographed extending transversely to a direction of scanning.

21. The apparatus as defined in claim 1 wherein said attenuating elements include juxtaposed coils each having a magnet pole with at least one row of magnet poles positioned parallel to said slit diaphragm, electric current flowing through each juxtaposed coil being determined by said planar X-ray beam to a greater or lesser extend in dependence on intensity of current thereto under the influence of an associated magnet pole.

22. The apparatus as defined in claim 21 wherein each coil is wound about a sleeve having an extended portion about a magnet pole to move relatively thereto.

23. The apparatus as defined in claim 21 wherein at least two rows of coils and associated magnet poles are arranged with one row of coils being staggered with reference to another row of coils.

24. The apparatus as defined in claim 21 wherein the magnet poles and the coils are inclined to the planar X-ray beam.

25. The apparatus as defined in claim 1 and further including end members to vary an effective length of said slit diaphragm in response to said control means.

26. The apparatus as defined in claim 1 wherein at least some of said attenuating elements are connected eccetrically through a connector to a shaft of a stepping motor, each stepping motor being controlled by said control means.

* * * * *